(12) United States Patent
Komoriya et al.

(10) Patent No.: US 7,781,602 B2
(45) Date of Patent: Aug. 24, 2010

(54) FLUORINATED CYCLIC COMPOUND, POLYMERIZABLE FLUOROMONOMER, FLUOROPOLYMER, RESIST MATERIAL COMPRISING THE SAME, AND METHOD OF FORMING PATTERN WITH THE SAME

(75) Inventors: Haruhiko Komoriya, Kawagoe (JP);
Shinichi Sumida, Kawagoe (JP);
Katsunori Kawamura, Kawagoe (JP);
Satoru Kobayashi, Kawagoe (JP);
Satoru Miyazawa, Kawagoe (JP);
Kazuhiko Maeda, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 75 days.

(21) Appl. No.: 11/941,433

(22) Filed: Nov. 16, 2007

(65) Prior Publication Data
US 2008/0194764 A1 Aug. 14, 2008

Related U.S. Application Data

(63) Continuation-in-part of application No. 10/553,600, filed as application No. PCT/JP2004/004007 on Mar. 24, 2004, now abandoned.

(30) Foreign Application Priority Data
Apr. 25, 2003 (JP) .............................. 2003-120921

(51) Int. Cl.
C07D 313/00 (2006.01)
C08F 214/26 (2006.01)
C08F 18/20 (2006.01)

(52) U.S. Cl. .................. 549/354; 525/200; 526/245
(58) Field of Classification Search ................ 549/354; 525/200; 526/245
See application file for complete search history.

(56) References Cited

U.S. PATENT DOCUMENTS

| 3,036,091 A | 5/1962 | England |
| 6,908,724 B2 * | 6/2005 | Araki et al. ............ 430/270.1 |

FOREIGN PATENT DOCUMENTS

| JP | 2003-2883 A | 1/2003 |
| JP | 2003-55362 A | 2/2003 |
| WO | WO 02/36533 A1 | 5/2002 |
| WO | WO 2004/014960 A2 | 2/2004 |

OTHER PUBLICATIONS

Dammel et al., "New Resin Systems for 157nm Lithography", Journal of Photopolymer Science and Technology, 2001, vol. 14, No. 4, pp. 603-611.
Fedynyshyn et al., "Fluoroaromatic Resists for 157-nm Lithography", Journal of Photopolymer Science and Technology, 2002, vol. 15, No. 4, pp. 655-666.
International Search Report dated May 25, 2004 (Two (2) pages).

* cited by examiner

*Primary Examiner*—D. Margaret Seaman
*Assistant Examiner*—Nizal S Chandrakumar
(74) *Attorney, Agent, or Firm*—Crowell & Moring LLP

(57) ABSTRACT

The present invention relates to a novel fluorine-containing cyclic compound that is derived from a norbornadiene and hexafluoroacetone and has an oxacyclopentane structure. This compound may be represented by the following formula (1) or (2). Furthermore, the present invention relates to a fluorine-containing polymer compound prepared by a polymerization or copolymerization using this fluorine-containing cyclic compound or its derivative. By using such fluorine-containing polymer compound, it is possible to provide a superior resist material and a fine pattern forming process using the same.

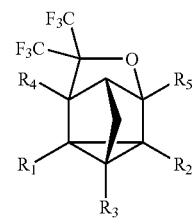

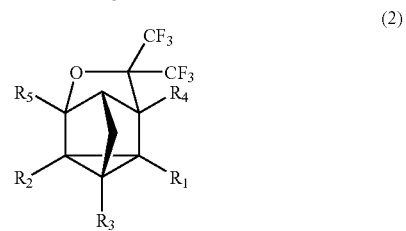

8 Claims, No Drawings

FLUORINATED CYCLIC COMPOUND, POLYMERIZABLE FLUOROMONOMER, FLUOROPOLYMER, RESIST MATERIAL COMPRISING THE SAME, AND METHOD OF FORMING PATTERN WITH THE SAME

BACKGROUND OF THE INVENTION

The present invention relates to novel fluorine-containing cyclic compounds and polymer compounds using the same and particularly to resist materials of vacuum ultraviolet region, which have recently and actively been studied, and pattern forming processes.

Fluorine-containing compounds have been used or developed in a wide applied field centered at advanced material fields due to characteristics possessed by fluorine, such as water repellency, oil repellency, low water absorption, heat resistance, weather resistance, corrosion resistance, transparency, photosensitivity, low refractive index, and low dielectric property. In particular, in the case of utilizing characteristics of transparency behavior in each wavelength, they are applied to the coating field. There are active researches and developments going on in the fields such as anti-reflection films, to which low refractive indexes and visible light transparency have been applied, optical devices, to which transparency in long wavelength band (optical communication wavelength band) has been applied, and resist materials, to which transparency in ultraviolet region (particularly vacuum ultraviolet wavelength region) has been applied. As a common high-molecule design in these applied fields, it is tried to achieve good adhesion to substrate and high glass transition point (hardness), while achieving transparency in each wavelength for use by introducing as many fluorine atoms as possible. There are various proposals of increasing transparency at each wavelength by increasing the fluorine content as material design. However, there are few examples on improving fluorine-containing monomers themselves in hydrophilicity and adhesion and on obtaining high Tg. Recently, in next generation $F_2$ resist field of vacuum ultraviolet region, there were reports on a hydroxyl-containing fluorostyrene (see T. H. Fedynyshyn, A. Cabral et al., J. Photopolym. Sci. Technol., 15, 655-666 (2002)) and on a hydroxyl-containing fluoronorbornene compound (see Ralph R. Dammel, Raj Sakamuri et al., J. Photopolym. Sci. Technol., 14, 603-611 (2001)). Thus, there was emerged an idea of containing fluorine and making polarity of hydroxyl group coexistent. However, compatibility between transparency in ultraviolet rays and etching resistance is still insufficient, and there exist many factors to be improved. Furthermore, with respect to polymerizability too, conventional fluorine-containing norbornene compounds have an electron-attracting group, such as fluorine atom and trifluoromethyl group, directly on the norbornene ring, thereby lowering electron density of a polymerizable double bond. Thus, there were problems of low yield and insufficient molecular weight in synthesis of polymer compounds. Thus, these conventional compounds are not necessarily sufficient in capability, and there has been a demand for creating a novel monomer or its raw material capable of efficiently providing further improved polymer compounds.

SUMMARY OF THE INVENTION

It is an object of the present invention to provide a novel fluorine-containing cyclic compound, a fluorine-containing polymerizable monomer and a fluorine-containing polymer compound, which have high transparency in a wide wavelength region from ultraviolet region to near infrared region, and a resist material, which has high adhesion to substrate and film-forming property and high etching resistance, and a pattern-forming process using the same.

As a result of a repeated eager examination to solve the above task, the present inventors have found a novel fluorine-containing cyclic compound having a oxacyclopentane structure derived from a norbornadiene and hexafluoroacetone. We have synthesized a fluorine-containing polymer compound polymerized or copolymerized using this fluorine-containing cyclic compound or its derivative. We have found a resist material having a high etching resistance and a pattern-forming process using that, by making it have a high fluorine content, a high transparency in a wide wavelength region from ultraviolet region to near infrared region, a high adhesion to substrate and a film-forming property, and a polycyclic structure, thereby completing the present invention.

That is, the present invention provides a fluorine-containing cyclic compound, a fluorine-containing polymerizable monomer, a fluorine-containing polymer compound and a resist material using that, and a pattern-forming process.

According to a first aspect of the present invention, there is provided a fluorine-containing cyclic compound represented by the following formula (1) or (2):

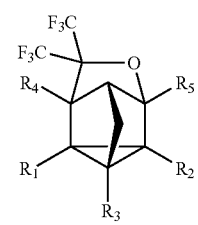

(1)

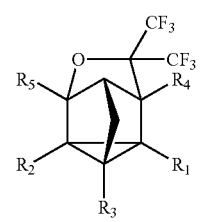

(2)

wherein, in the formulas (1) and (2), each of R1, R2, R3, R4 and R5 is independently selected from the group consisting of hydrogen, alkyl group, hydroxyl group, halogen atom, halogenated alkyl group, carbinol group, and hexafluorocarbinol group; wherein the hexafluorocarbinol group contained in the formula may be partially or entirely protected; and wherein the protecting group is a straight-chain, branched or cyclic hydrocarbon group of a carbon number of 1-25 or a group containing an aromatic hydrocarbon group and may contain at least one of fluorine atom, oxygen atom, nitrogen atom, and carbonyl bond.

According to a second aspect of the present invention, there is provided a fluorine-containing cyclic compound represented by the following structural formula (3) or (4).

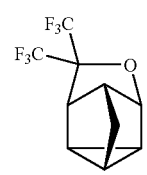

(3)

-continued

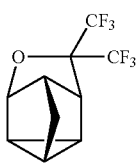 (4)

According to a third aspect of the present invention, there is provided a fluorine-containing cyclic compound represented by one of the following structural formulas (5) to (8).

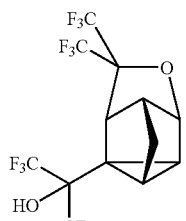 (5)

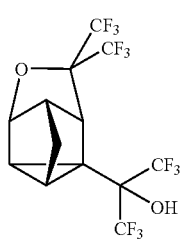 (6)

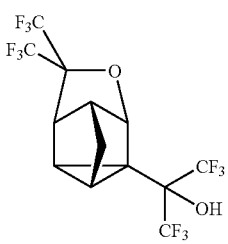 (7)

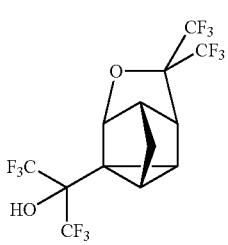 (8)

According to a fourth aspect of the present invention, there is provided a fluorine-containing cyclic compound that is represented by the following formula (9) or (10) and is derived from a fluorine-containing cyclic compound represented by one of the formulas (1) to (8).

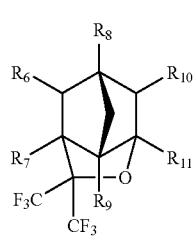 (9)

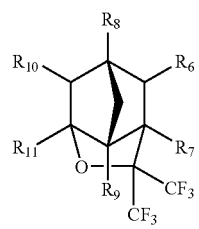 (10)

wherein, in the formulas (9) and (10), each of R6, R7, R8, R9, R10 and R11 is independently selected from the group consisting of hydrogen, alkyl group, halogenated alkyl group, hydroxyl group, alkyloxy group, halogenated alkyloxy group, mercapto group, alkylthio group, halogenated alkylthio group, sulfoxy group, alkylsulfonyloxy group, halogenated alkylsulfonyloxy group, alkylsilyl group, halogenated alkylsilyl group, alkoxysilyl group, halogen atom, amino group, alkylamino group, carbinol group, and hexafluorocarbinol group; wherein the hexafluorocarbinol group contained in the formula may be partially or entirely protected; and wherein the protecting group is a straight-chain, branched or cyclic hydrocarbon group of a carbon number of 1-25 or a group containing an aromatic hydrocarbon group and may contain at least one of fluorine atom, oxygen atom, nitrogen atom, and carbonyl bond.

According to a fifth aspect of the present invention, there is provided a fluorine-containing cyclic compound represented by one of the following structural formulas (13) to (16).

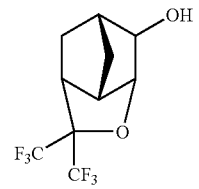 (13)

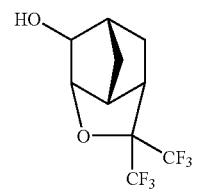 (14)

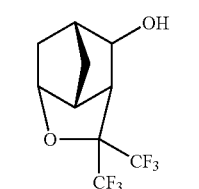 (15)

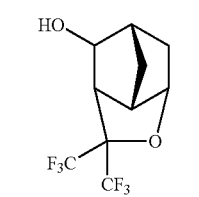 (16)

According to a sixth aspect of the present invention, there is provided a fluorine-containing cyclic compound represented by one of the following structural formulas (17) to (20).

(17)
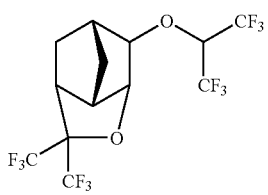

(18)
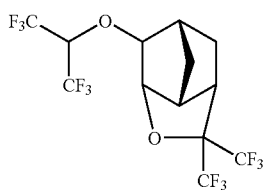

(19)
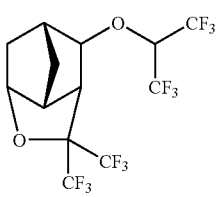

(20)
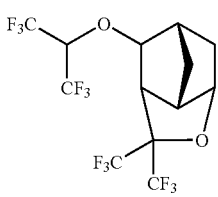

According to a seventh aspect of the present invention, there is provided a fluorine-containing cyclic compound represented by one of the following structural formulas (21) to (24).

(21)
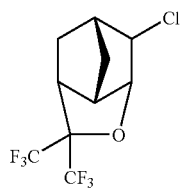

(22)
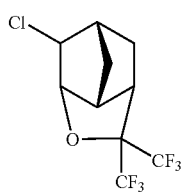

-continued

(23)
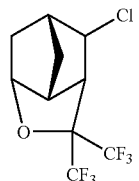

(24)
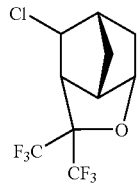

According to an eighth aspect of the present invention, there is provided a fluorine-containing cyclic compound having at least one hydroxyl group or hexafluorocarbinol group and represented by the following structural formula (25) or (26).

(25)
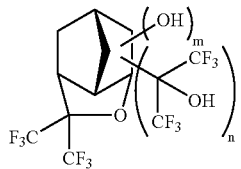

(26)
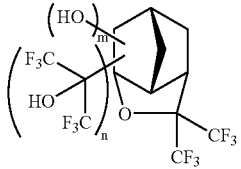

wherein, in the structural formulas (25) and (26), "m+n" represents an integer of 1 to 4; wherein the hydroxyl group and the hexafluorocarbinol group contained in the formula may be partially or entirely protected; and the protecting group is a straight-chain, branched or cyclic hydrocarbon group of a carbon number of 1-25 or a group containing an aromatic hydrocarbon group and may contain at least one of fluorine atom, oxygen atom, nitrogen atom, and carbonyl bond.

According to a ninth aspect of the present invention, there is provided a fluorine-containing polymerizable monomer that is represented by the following formula (27) or (28) and is derived from a fluorine-containing cyclic compound represented by one of the formulas (1) to (26).

(27)
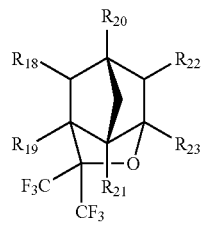

-continued (28)

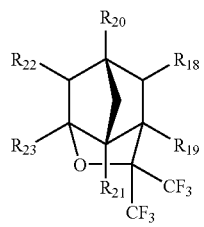

wherein, in the formulas (27) and (28), one of R18, R19, R20, R21, R22 and R23 is a polymerizable group represented by the formula (29); wherein of R18, R19, R20, R21, R22 and R23, groups other than the polymerizable group are selected from the group consisting of hydrogen, alkyl group, halogenated alkyl group, hydroxyl group, alkyloxy group, halogenated alkyloxy group, mercapto group, alkylthio group, halogenated alkylthio group, sulfoxy group, alkylsulfonyloxy group, halogenated alkylsulfonyloxy group, alkylsilyl group, halogenated alkylsilyl group, alkoxysilyl group, halogen atom, amino group, alkylamino group, carbinol group, and hexafluorocarbinol group; wherein the hexafluorocarbinol group contained in the formulas (27) and (28) may be partially or entirely protected; wherein the protecting group is a straight-chain, branched or cyclic hydrocarbon group of a carbon number of 1-25 or a group containing an aromatic hydrocarbon group and may contain at least one of fluorine atom, oxygen atom, nitrogen atom, and carbonyl bond; wherein, in the formula (29), each of R24, R25 and R26 is independently a hydrogen atom, a fluorine atom or a straight-chain, branched or cyclic alkyl group or fluorinated alkyl group having a carbon number of 1-25; and wherein R27 represents a single bond or methylene group, a straight-chain, branched or cyclic alkylene group of a carbon number of 2-20, a straight-chain, branched or cyclic alkylene group of a carbon number of 2-20, an oxygen atom, a sulfur atom, —(C=O)O—, —O(C=O)—, or dialkylsilylene group.

(29)

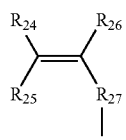

According to a tenth aspect of the present invention, there is provided a fluorine-containing polymerizable monomer represented by the following structural formulas (30) to (33).

(30)

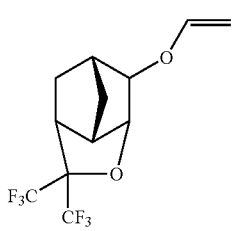

(31)

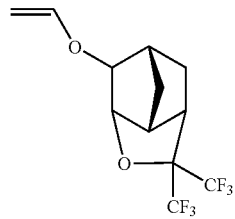

(32)

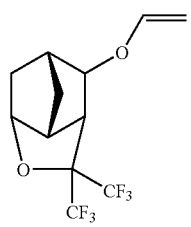

(33)

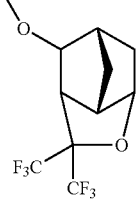

According to an eleventh aspect of the present invention, there is provided a fluorine-containing polymerizable monomer represented by the following structural formulas (34) to (37).

(34)

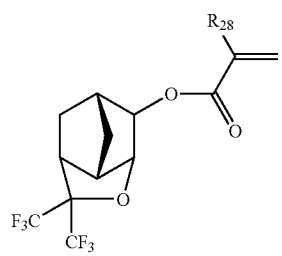

(35)

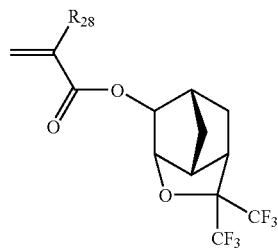

(36)

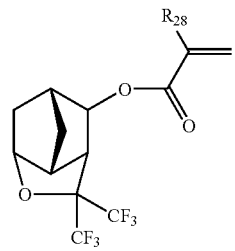

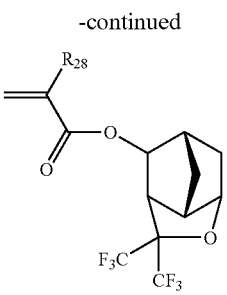

(37)

In the formulas (34) to (37), each R28 independently represents a hydrogen, methyl group, fluorine, or trifluoromethyl group.

According to a twelfth aspect of the present invention, there is provided a fluorine-containing cyclic compound represented by the following structural formula (38) or (39) and having at least one polymerizable group.

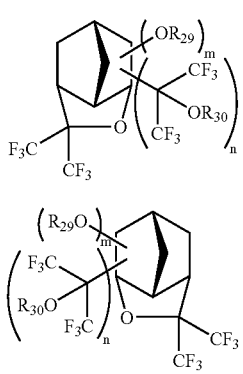

(38)

(39)

wherein, in the structural formulas (38) and (39), "m+n" represents an integer of 1 to 4. At least one of R29 and R30 is a polymerizable group represented by the formula (40); wherein, of R29 and R30, a group other than the polymerizable group represents a hydrogen or protecting group; and the protecting group is a straight-chain, branched or cyclic hydrocarbon group of a carbon number of 1-20 or a group containing an aromatic hydrocarbon group and may contain at least one of fluorine atom, oxygen atom, nitrogen atom, and carbonyl bond; wherein, in the following formula (40), each of R31, R32 and R33 is independently a hydrogen atom, fluorine atom, or a straight-chain, branched or cyclic alkyl group or fluorinated alkyl group of a carbon number of 1-25; and wherein R34 represents a single bond or methylene group, a straight-chain, branched or cyclic alkylene group of a carbon number of 2-20, a straight-chain, branched or cyclic fluorinated alkylene group, a carbonyl group or dialkylsilylene group.

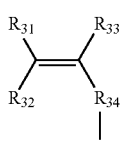

(40)

DETAILED DESCRIPTION

The present invention provides novel fluorine-containing cyclic compounds, fluorine-containing polymerizable monomers, and fluorine-containing polymer compounds. Polymer compounds synthesized by using the novel fluorine-containing cyclic compounds have high transparency in a wide wavelength region from ultraviolet region to near infrared region, are suitable for resist materials having high adhesion to substrate and film-forming property and high etching resistance, and are particularly suitable for photoresist materials of vacuum ultraviolet region. Furthermore, a pattern-forming process using them is suitable for forming patterns of high resolution.

In the following, fluorine-containing cyclic compounds of the present invention are explained. A compound represented by the formula (1) or (2) of the present invention is a novel fluorine-containing cyclic compound having an oxacyclopentane structure and derived from a norbornadiene and hexafluoroacetone.

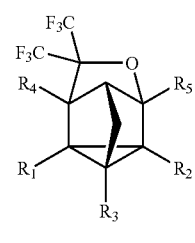

(1)

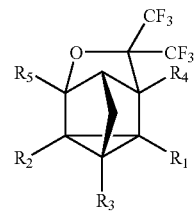

(2)

In general, it is known that, as the fluorine content increases, transparency improves in a wide wavelength region from ultraviolet region to near infrared region and that lowering of refractive index is caused. On the other hand, as the fluorine content increases, lowering of adhesion with substrate and lowering of film-forming property are also caused. However, the compound represented by the formula (1) or (2), due to having an oxycyclopentane structure, has made it possible to make a polymer compound derived from this have a high adhesion with substrate and a high film-forming property. The polycyclic skeleton contributes to etching resistance that is necessary for resist materials.

In the compound represented by the formula (1) or (2) according to the present invention, each of R1, R2, R3, R4 and R5 is independently a hydrogen, alkyl group, hydroxyl group, halogen atom, halogenated alkyl group, carbinol group, or hexafluorocarbinol group. In case that it is used as a polymer material through a polymerization reaction, as the carbon number of the substituent increases, there occur lowering of polymerizability due to steric hindrance, lowering of transparency, and increase of refractive index. Therefore, the carbon number is more preferably 1-5. For example, methyl group, ethyl group, n-propyl group, iso-propyl group, n-butyl group, sec-butyl group, tert-butyl group and the like are cited. The hydrogen atoms may be partially or entirely replaced with fluorine atoms. Hexafluorocarbinol group is preferably used due to its high fluorine content.

In case that a hexafluorocarbinol group is contained in the formula (1) or (2), it may be partially or entirely protected. The protecting group is a straight-chain, branched or cyclic hydrocarbon group of a carbon number of 1-25 or an aromatic hydrocarbon group. It can be exemplified by methyl group, ethyl group, propyl group, isopropyl group, cyclopropyl group, n-propyl group, iso-propyl group, sec-butyl group, tert-butyl group, n-pentyl group, cyclopentyl group, sec-pentyl group, neopentyl group, hexyl group, cyclohexyl group, ethylhexyl group, norbornel group, adamantyl group, vinyl group, allyl group, butenyl group, pentenyl group, ethynyl group, phenyl group, benzyl group, and 4-methoxybenzyl group. The above functional group may be partially or entirely replaced with fluorine atoms. As one containing oxygen atom, it is possible to cite alkoxycarbonyl group, acetal group, acyl group and the like. The alkoxycarbonyl group can be exemplified by tert-butoxycarbonyl group, tert-amyloxycarbonyl group, methoxycarbonyl group, ethoxycarbonyl group, i-propoxycarbonyl group and the like. As the acetal group, there are cited acyclic ethers, such as methoxymethyl group, methoxyethoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group and ethoxyisobutyl group, and cyclic ethers, such as tetrahydrofuranyl group and tetrahydropyranyl group. As the acyl group, it is possible to cite acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, and the like. Furthermore, it is possible to use ones in which hydrogen atoms of the above substituents have been partially or fully replaced with fluorine atoms.

The compounds represented by the formulas (9) and (10) of the present invention are fluorine-containing cyclic compounds having oxacyclopentane structures. These compounds can be derived from fluorine-containing cyclic compounds represented by the formulas (1) to (8).

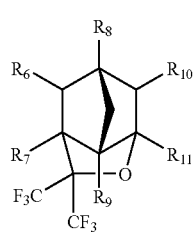

(9)

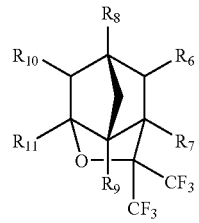

(10)

These compounds contain many fluorines in the molecules similar to the compound described as the above formula (1) or (2) and at the same time have an oxacyclopentane structure. Therefore, they are high in transparency in a wide wavelength region and are superior in adhesion to substrate. This advantageous effect is assumed to be due to that an unshared electron pair on the oxygen of the oxacyclopentane ring is oriented to the outside of the molecule. The skeleton formed of the norbornane or the norbornane and the oxacyclopentane contributes to etching resistance necessary for resist material. In the formulas (9), (10), (11) and (12), each of R6, R7, R8, R9, R10, R11, R12, R13, R14, R15, R16 and R17 is selected from the group consisting of hydrogen, alkyl group, halogenated alkyl group, hydroxyl group, alkyloxy group, halogenated alkyloxy group, mercapto group, alkylthio group, halogenated alkylthio group, sulfoxy group, alkylsulfonyloxy group, halogenated alkylsulfonyloxy group, alkylsilyl group, halogenated alkylsilyl group, alkoxysilyl group, halogen atom, amino group, alkylamino group, carbinol group, and hexafluorocarbinol group. The hexafluorocarbinol group contained in the formulas may be partially or entirely protected. The protecting group is a straight-chain, branched or cyclic hydrocarbon group of a carbon number of 1-25 or a group containing an aromatic hydrocarbon group. It is the same as one exemplified as the protecting group of the hexafluorocarbinol group contained in the formula (1) or (2).

The compounds represented by the formulas (27) and (28) of the present invention are fluorine-containing polymerizable monomers. These compounds can be derived from the fluorine-containing cyclic compounds represented by the formulas (1) to (10) and (13) to (26).

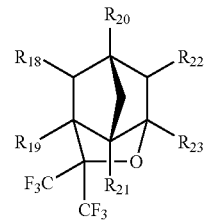

(27)

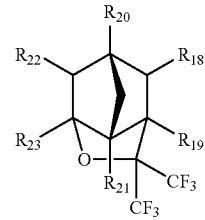

(28)

In the formulas (27) and (28), one of R18, R19, R20, R21, R22 and R23 is a polymerizable group represented by the formula (29). Of R18, R19, R20, R21, R22 and R23, groups other than the polymerizable group are selected from the group consisting of hydrogen, alkyl group, halogenated alkyl group, hydroxyl group, alkyloxy group, halogenated alkyloxy group, mercapto group, alkylthio group, halogenated alkylthio group, sulfoxy group, alkylsulfonyloxy group, halogenated alkylsulfonyloxy group, alkylsilyl group, halogenated alkylsilyl group, alkoxysilyl group, halogen atom, amino group, alkylamino group, carbinol group, and hexafluorocarbinol group. The hexafluorocarbinol group contained in the formulas (27) and (28) may be partially or entirely protected. The protecting group is a straight-chain, branched or cyclic hydrocarbon group of a carbon number of 1-25 or a group containing an aromatic hydrocarbon group. It may contain at least one of fluorine atom, oxygen atom, nitrogen atom, and carbonyl bond. In the formula (29), each of R24, R25 and R26 is independently a hydrogen atom, a fluorine atom or a straight-chain, branched or cyclic alkyl group or fluorinated alkyl group having a carbon number of 1-25. R27 represents a single bond or methylene group, a straight-chain, branched or cyclic alkylene group of a carbon number of 2-20, a straight-chain, branched or cyclic alkylene group of a carbon number of 2-20, an oxygen atom, a sulfur atom, —(C═O)O—, —O(C═O)—, or dialkylsilylene group.

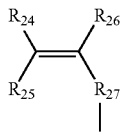

(29)

As the polymerizable group is exemplified, there are cited vinyl group, allyl group, acryloyl group, methacryloyl group, fluorovinyl group, difluorovinyl group, trifluorovinyl group, difluorotrifluoromethylvinyl group, trifluoroallyl group, perfluoroallyl group, trifluoromethylacryloyl group, nonylfluorobutylacryloyl group, vinyl ether group, fluorine-containing vinyl ether group, allyl ether group, fluorine-containing allyl ether group and the like. Acryloyl group, methacryloyl group, trifluoromethylacryloyl group, and vinyl ether group can preferably be used, due to their high polymerizability and their high copolymerizability with other monomers. A functional group containing fluorine atom is applied in order to further provide transparency and low refractive index.

An acid-labile group usable in the present invention can be used without particular limitation, as long as it is a group that is released by the effect of an optical acid generator, hydrolysis or the like. As specific examples are cited, it is possible to cite alkoxycarbonyl group, acetal group, silyl group, acyl group, and the like. The alkoxycarbonyl group can be exemplified by tert-butoxycarbonyl group, tert-amyloxycarbonyl group, methoxycarbonyl group, ethoxycarbonyl group, and i-propoxycarbonyl group. As the acetal group, it is possible to cite methoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group, ethoxyisobutyl group, and the like. It is also possible to use an acetal group formed by the addition of a vinyl ether to a hydroxyl group. As the silyl group, it is possible to cite, for example, trimethylsilyl group, ethyldimethylsilyl group, methyldiethylsilyl group, triethylsilyl group, i-propyldimethylsilyl group, methyldi-i-propylsilyl group, tri-i-propylsilyl group, t-butyldimethylsilyl group, methyldi-t-butylsilyl group, tri-t-butylsilyl group, phenyldimethylsilyl group, methyldiphenylsilyl group, and triphenylsilyl group. As the acyl group, it is possible to cite acetyl group, propionyl group, butyryl group, heptanoyl group, hexanoyl group, valeryl group, pivaloyl group, isovaleryl group, lauryloyl group, myristoyl group, palmiotyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, and the like. Furthermore, it is also possible to use ones in which hydrogen atoms of these acid-labile groups have been partially or fully replaced with fluorine atoms.

It is an object of using an acid-labile group to achieve positive-type photosensitivity and solubility in an alkali aqueous solution after exposure to high-energy rays, such as far ultraviolet rays of 300 nm or less in wavelength, excimer laser, and X rays, or to electron beam. One having fluorine atom in the functional group is to provide transparency, and one having a cyclic structure is to further provide characteristics such as etching resistance and high glass transition point. They can be used properly depending on the applied field of the present invention.

Next, the polymer compounds according to the present invention are explained. The polymer compounds of the present invention are polymer compounds obtained by a homopolymerization or copolymerization of the fluorine-containing cyclic compounds represented by the structural formulas (27), (28) and (30) to (39).

As a monomer that is copolymerizable with the fluorine-containing cyclic compound of the present invention is specifically exemplified, there are cited maleic anhydride, acrylic esters, fluorine-containing acrylic esters, methacrylic esters, fluorine-containing methacrylic esters, styrene compounds, fluorine-containing styrene compounds, vinyl ethers, fluorine-containing vinyl ethers, allyl ethers, fluorine-containing allyl ethers, olefins, fluorine-containing olefins, norbornene compounds, fluorine-containing norbornene compounds, sulfur dioxide, and vinyl silanes.

Acrylic esters or methacrylic esters that are usable in the present invention can be used without particular limitation with respect to ester side chains. As known compounds are specified, it is possible to use alkyl esters of acrylic acid or methacrylic acid, such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate, and 2-hydroxypropyl acrylate or methacrylate; acrylates or methacrylates containing ethylene glycol, propylene glycol and tetramethylene glycol; unsaturated amides such as acrylic amide, methacrylic amide, N-methylolacrylic amide, N-methylolmethacrylic amide and diacetoneacrylic amide; acrylonitrile, methacrylonitrile, alkoxysilane-containing vinyl silanes, acrylic or methacrylic esters, tert-butyl acrylate or methacrylate, 3-oxocyclohexyl acrylate or methacrylate, adamantyl acrylate or methacrylate, alkyladamantyl acrylate or methacrylate, cyclohexyl acrylate or methacrylate, tricyclodecanyl acrylate or methacrylate, acrylates or methacrylates having cyclic structures such as lactone ring and norbornene ring, acrylic acid, methacrylic acid, and the like. Furthermore, it is also possible to copolymerize the above acrylate compounds containing a cyano group at α-position and analogous compounds such as maleic acid, fumaric acid and maleic anhydride.

A fluorine-containing acrylic ester and a fluorine-containing methacrylic ester usable in the present invention is a monomer containing a fluorine atom or fluorine-containing group at the acrylic α-position, or an acrylic ester or methacrylic ester having a fluorine-containing substituent at the ester moiety. A fluorine-containing compound containing fluorine at α-position and ester moiety is also preferable. A cyano group may be introduced into α-position. For example, as a monomer in which a fluorine-containing alkyl group has been introduced into α-position, there is preferably used a monomer in which the above-mentioned non-fluoric acrylic ester or methacrylic ester has been provided at α-position with trifluoromethyl group, trifluoroethyl group, nonafluoro-n-butyl group or the like. The ester moiety in that case is not necessarily required to contain fluorine. In case that α-trifluoromethylacrylic alkyl ester is used as a copolymerizing component, the polymer yield is relatively high, and solubility of the obtained polymer in organic solvent is good. Therefore, it is preferably used.

On the other hand, the monomer containing fluorine at its ester moiety is an acrylic ester or methacrylic ester having a unit in which a fluorine alkyl group that is a perfluoroalkyl group or fluoroalkyl group is contained as ester moiety or in which a cyclic structure and fluorine atom are coexistent. The cyclic structure is, for example, a fluorine-containing benzene ring, fluorine-containing cyclopentane ring, fluorine-containing cyclohexane ring, fluorine-containing cycloheptane ring or the like, in which a fluorine atom, trifluoromethyl group, hexafluorocarbinol group or the like has been substituted. It is possible to use an acrylic or methacrylic ester having an ester moiety that is a fluorine-containing t-butyl ester group. It is also possible to use monomers in which these fluorine-containing functional groups are used together with fluorine-containing alkyl groups at α-position. Of such units, as particularly representative ones are exemplified in the form of monomer, there are cited 2,2,2-trifluoroethylacrylate, 2,2,3,3-tetrafluoropropylacrylate, 1,1,1,3,3,3-hexafluoroisopropylacrylate, heptafluoroisopropylacrylate, 1,1-dihydroheptafluoro-n-butylacrylate, 1,1,5-trihydrooctafluoro-n-pentylacrylate, 1,1,2,2-tetrahydrotridecafluoro-n-octylacrylate, 1,1,2,2-tetrahydroheptadecafluoro-n-decylacrylate, 2,2,2-trifluoroethylmethacrylate, 2,2,3,3-tetrafluoropropylmethacrylate, 1,1,1,3,3,3-hexafluoroisopropylmethacrylate, heptafluoroisopropylmethacrylate, 1,1-dihydroheptafluoro-n-butylmethacrylate, 1,1,5-trihydrooctafluoro-n-pentylmethacrylate, 1,1,2,2-tetrahydrotridecafluoro-n-octylmethacrylate, 1,1,2,2-tetrahydroheptadecafluoro-n-decylmethacrylate, perfluorocyclohexylmethylacrylate, perfluorocyclohexylmethylmethacrylate, 6-[3,3,3-trifluoro-2-hydroxy-2-(trifluoromethyl)propyl]bicyclo[2.2.1]heptyl-2-ylacrylate, 6-[3,3,3-trifluoro-2-hydroxy-2-(trifluoromethyl)propyl]bicyclo[2.2.1]heptyl-2-yl-2-(trifluoromethyl) acrylate, 6-[3,3,3-trifluoro-2-hydroxy-2-(trifluoromethyl) propyl]bicyclo[2.2.1]heptyl-2-ylmethacrylate, 1,4-bis(1,1,1,3,3,3-hexafluoro-2-hydroxyisopropyl)cyclohexylacrylate, 1,4-bis(1,1,1,3,3,3-hexafluoro-2-hydroxyisopropyl)cyclohexylmethacrylate, 1,4-bis(1,1,1,3,3,3-hexafluoro-2-hydroxyisopropyl)cyclohexyl-2-trifluoromethylacrylate, and the like.

Furthermore, as styrene compounds and fluorine-containing styrene compounds usable in the present invention, it is possible to use compounds, in which one or plurality of hexafluorocarbinol groups or functional groups obtained by modifying their hydroxyl groups are bonded, as well as styrene, fluorinated styrene, hydroxystyrene and the like. In other words, it is possible to preferably use a styrene or hydroxystyrene containing fluorine atom or trifluoromethyl group substituted for hydrogen, the above styrene having a halogen, alkyl group or fluorine-containing alkyl group bonded to α-position, a perfluorovinyl-containing styrene, and the like.

As the vinyl ethers, the fluorine-containing vinyl ethers, the allyl ethers and the fluorine-containing allyl ethers, it is possible to use alkyl vinyl ethers or alkyl allyl ethers optionally containing methyl group, ethyl group, propyl group, butyl group, and hydroxyl group such as hydroxyethyl group and hydroxybutyl group. It is also possible to use a cyclic vinyl or allyl ether containing a cyclohexyl group, norbornel group, aromatic ring or a hydrogen or carbonyl bond in its cyclic structure, and a fluorine-containing vinyl ether or fluorine-containing allyl ether containing fluorine atoms partially or fully substituted for hydrogen of the above functional group.

Furthermore, it is possible to use vinyl esters, vinyl silanes, olefins, fluorine-containing olefins, norbornene compounds, fluorine-containing norbornene compounds, and other compounds containing polymerizable unsaturated bonds, without particular limitations.

The olefin can be exemplified by ethylene, propylene, isobutene, cyclopentene, and cyclohexene. The fluorine-containing olefin can be exemplified by vinyl fluoride, vinylidene fluoride, trifluoroethylene, chlorotrifluoroethylene, tetrafluoroethylene, hexafluoropropylene, and hexafluoroisobutene.

The norbornene compounds and the fluorine-containing norbornene compounds are norbornene monomers having a mononucleus or multinucleus structure. Upon this, fluorine-containing olefin, allyl alcohol, fluorine-containing allyl alcohol, homoallyl alcohol, fluorine-containing homoallyl alcohol produce norbornene compounds that are formed by a Diels-Alder addition reaction of unsaturated compounds, such as acrylic acid, α-fluoroacrylic acid, α-trifluoromethylacrylic acid, methacrylic acid, all of acrylic esters, methacrylic esters, fluorine-containing acrylic esters or fluorine-containing methacrylic esters, which have been mentioned in the present specification, 2-(benzoyloxy)pentafluoropropane, 2-(methoxyethoxymethyloxy)pentafluoropropene, 2-(tetrahydroxypyranyloxy)pentafluoropropene, 2-(benzoyloxy)trifluoroethylene, and 2-(methoxymethyloxy)trifluoroethylene, with cyclopentadiene and cyclohexadiene. It can be exemplified by 3-(5-bicyclo[2.2.1]heptene-2-yl)-1,1,1-trifluoro-2-(trifluoromethyl)-2-propanol and the like. The above copolymerizable compounds may be used singly or in a combination of at least two types.

In the polymerization or copolymerization of the present invention, although the ratio of the fluorine-containing compound to the comonomer is not particularly limited, it is preferably selected in a range of 10 to 100%. More preferably, it is 30 to 100%. If it is less than 30%, sufficient transparency and film-forming property are not achieved depending on the wavelength range of the applied field.

The polymerization process of the polymer compound according to the present invention is not particularly limited, as long as it is a process generally used. Radical polymerization, ionic polymerization and the like are preferable. In some cases, it is also possible to use coordinated anionic polymerization, living anionic polymerization, cationic polymerization, ring-opening metathesis polymerization, vinylene polymerization and the like.

The radical polymerization can be conducted by a known polymerization process such as bulk polymerization, solution polymerization, suspension polymerization or emulsion polymerization, in the presence of a radical polymerization initiator or radical initiating source, by a batch-wise, half-continuous or continuous operation.

The radical polymerization initiator is not particularly limited. As examples, azo compounds, peroxides and redox compounds are cited. In particular, azobisisobutyronitrile, t-butylperoxypivalate, di-t-butylperoxide, i-butyrylperoxide, lauroylperoxide, succinic acid peroxide, dicinnamylperoxide, di-n-propylperoxydicarbonate, t-butylperoxyallyl monocarbonate, benzoyl peroxide, hydrogen peroxide, ammonium persulfate and the like are preferable.

The reaction vessel used in the polymerization is not particularly limited. In the polymerization, it is optional to use a polymerization solvent. As the polymerization solvent, one that does not interfere with the radical polymerization is preferable. Its representative ones are esters such as ethyl acetate and n-butyl acetate; ketones such as acetone and methyl isobutyl ketone; hydrocarbons such as toluene and cyclohexane; and alcohol solvents such as methanol, isopropyl alcohol and ethylene glycol monomethyl ether. Furthermore, it is also possible to use various solvents such as water, ethers, cyclic ethers, fluorohydrocarbons, and aromatics. These solvents can be used singly or in a mixture of at least two kinds. Furthermore, it is possible to use a molecular weight adjusting agent such as mercaptan. The reaction temperature of the copolymerization is suitably changed depending on the radical polymerization initiator or radical polymerization initiating source. It is generally preferably 20-200° C., particularly preferably 30-140° C.

On the other hand, the ring-opening metathesis polymerization may be conducted in the presence of a cocatalyst using a transition metal catalyst of the groups 4 to 7 of the periodic table. It may be conducted by a known process in the presence of solvent.

The polymerization catalyst is not particularly limited. As examples, Ti, V, Mo and W catalysts are cited. In particular, titanium (IV) chloride, vanadium (IV) chloride, vanadium trisacetylacetonato, vanadium bisacetylacetonatodichloride, molybdenum (VI) chloride, and tungsten (VI) chloride and the like are preferable. The catalyst amount is from 10 mol % to 0.001 mol %, preferably 1 mol % to 0.01 mol %, relative to the used monomer.

As the cocatalyst, alkylaluminum, alkyltin and the like are cited. In particular, it can be exemplified by aluminum-based ones such as trialkylaluminums such as trimethylaluminum, triethylaluminum, tripropylaluminum, triisopropylaluminum, triisobutylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum, and trioctylaluminum; dialkylaluminum halides dimethylaluminum chloride, diethylaluminum chloride, diisopropylaluminum chloride, and diisobutylaluminumchloride; monoalkylaluminum halides such as methylaluminum dichloride, ethylaluminum dichloride, ethylaluminum diiodide, propylaluminum dichloride, isopropylaluminum dichloride, butylaluminum dichloride, and isobutylaluminum dichloride; and alkylaluminum sesquichlorides such as methylaluminum sesquichloride, ethylaluminum sesquichloride, propylaluminum sesquichloride; and isobutylaluminum sesquichloride; tetra-n-butyltin, tetraphenyltin, and triphenylchlorotin. The amount of the cocatalyst is by molar ratio 100 equivalents or less, preferably 30 equivalents or less, relative to the transition metal catalyst.

The polymerization solvent will do, as long as it does not interfere with the polymerization. As its representative ones, it can be exemplified by aromatic hydrocarbons such as benzene, toluene, xylene, chlorobenzene and dichlorobenzene; hydrocarbons such as hexane, heptane and cyclohexane; and halogenated hydrocarbons such as carbon tetrachloride, chloroform, methylene chloride and 1,2-dichloroethane. These solvents may be used alone or in a mixture of at leas two kinds. The reaction temperature is generally preferably −70° C. to 200° C., particularly preferably −30° C. to 60° C.

The vinylene polymerization may be conducted in the presence of a cocatalyst using a transition metal catalyst of the groups 8 to 10 of the periodic table, such as iron, nickel, rhodium, palladium and platinum, or a metal catalyst of the groups 4 to 6 of the periodic table, such as zirconium, titanium, vanadium, chromium, molybdenum, and tungsten. It may be conducted in the presence of a solvent using a known process.

The polymerization catalyst is not particularly limited. As examples, particularly, there are preferable transition metal compounds of the groups 8 to 10 of the periodic table such as iron(II) chloride, iron(III) chloride, iron(II) bromide, iron(III) bromide, iron(II) acetate, iron(III) acetylacetate, ferrocene, nickelocene, nickel(II) acetate, nickel bromide, nickel chloride, dichlorohexylnickel acetate, nickel lactate, nickel oxide, nickel tetrafluoroborate, bis(allyl)nickel, bis(cyclopentadienyl)nickel, nickel(II) hexafluoroacetylacetonatotetrahydrate, nickel(II) trifluoroacetylacetonatodihydrate, nickel(II) acetylacetonatotetrahydrate, rhodium(III) chloride, rhodium tris(triphenylphosphine)trichloride, palladium(II) bis(trifluoroacetate), palladium(II) bis(acetylacetonato), palladium(II) 2-ethylhexanoate, palladium(II) bromide, palladium(II) chloride, palladium(II) iodide, palladium(II) oxide, monoacetonitriletris(triphenylphosphine)palladium(II) tretrafluoroborate, tetrakis(acetonitrile)palladium(II) tetrafluoroborate, dichlorobis(acetonitrile)palladium(II), dichlorobis(triphenylphosphine)palladium(II), dichlorobis(benzonitrile)palladium(II), palladium acetylacetonato, palladium bis(acetonitrile)dichloride, palladium bis(dimethylsulfoxide)dichloride and platinum bis(triethylphosphine) hydrobromide, and transition metal compounds of the groups 4 to 6 of the periodic table such as vanadium(IV) chloride, vanadium trisacetylacetonato, vanadium bisacetylacetonatodichloride, trimethoxy(pentamethylcyclopentadienyl)titanium(IV), bis(cyclopentadienyl)titanium dichloride, and bis(cyclopentadienyl)zirconium dichloride. The catalyst amount is from 10 mol % to 0.001 mol %, preferably from 1 mol % to 0.01 mol %, relative to the used monomer.

As the cocatalyst, alkylaluminoxane, alkylaluminum and the like are cited. In particular, it can be exemplified by methylaluminoxane (MAO), trialkylaluminums such as trimethylaluminum, triethylaluminum, tripropylaluminum, triisopropylaluminum, triisobutylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum, and trioctylaluminum; dialkylaluminum halides such as dimethylaluminum chloride, diethylaluminum chloride, diisopropylaluminum chloride, and diisobutylaluminum chloride; monoalkylaluminum halides such as methylaluminum dichloride, ethylaluminum dichloride, ethylaluminum diiodide, propylaluminum dichloride, isopropylaluminum dichloride, butylaluminum dichloride, and isobutylaluminum dichloride; and alkylaluminum sesquichlorides such as methylaluminum sesquichloride, ethylaluminum sesquichloride, propylaluminum sesquichloride, and isobutylaluminum sesquichloride. The amount of the cocatalyst is 50 to 500 equivalents in terms of Al conversion in the case of methylaluminoxane. In the case of other alkylaluminums, it is 100 equivalents or less, preferably 30 equivalents or less, relative to 1 equivalent of the transition metal catalyst.

The polymerization solvent will do as long as it does not interfere with the polymerization. As representative ones, it can be exemplified by aromatic hydrocarbons such as benzene, toluene, xylene, chlorobenzene, and dichlorobenzene; hydrocarbons such as hexane, heptane, and cyclohexane; halogenated hydrocarbons such as carbon tetrachloride, chloroform, methylene chloride, and 1,2-dichloroethane; dimethylformamide, N-methylpyrolidone, and N-cyclohexylpyrolidone. These solvents may be used alone or in a mixture of at least two kinds. The reaction temperature is generally preferably −70° C. to +200° C., particularly preferably −40° C. to +80° C.

As a process of removing an organic solvent or water as the medium from the thus obtained solution or dispersion of the polymer compound according to the present invention, any known process can be used. For example, it is a process such as reprecipitation filtration or heated distillation under reduced pressure.

Number average molecular weight of the polymer compound of the present invention is generally 1,000 to 100,000. Preferably, a range of 3,000 to 50,000 is appropriate.

Next, the application field of the present invention is described. The present invention is based on the coating use. In general, the polymer compound of the present invention is dissolved in an organic solvent and formed into a film in its application. Therefore, the organic solvent to be used is not particularly limited, as long as the polymer compound is soluble. It is possible to use ketones such as acetone, methyl ethyl ketone, cyclohexanone, methyl isoamyl ketone and 2-heptanone; polyhydric alcohols such as ethylene glycol, ethylene glycol monoacetate, diethylene glycol, diethylene glycol monoacetate, propylene glycol, propylene glycol monoacetate, dipropylene glycol, or monomethyl ether, monoethyl ether, monopropyl ether, monobutyl ether or monophenyl ether) of dipropylene glycol monoacetate, and their derivatives; cyclic ethers such as dioxane; esters such as methyl lactate, ethyl lactate, methyl acetate, ethyl acetate, butyl acetate, methyl pyruvate, ethyl pyruvate, methyl methoxypropionate, and ethyl ethoxypropionate; aromatic solvents such as xylene and toluene; fluorine-containing solvents such as fleon, alternative fleon, perfluoro compounds, and hexafluoroisopropyl alcohol; and terpene-based petroleum naphtha solvents and paraffinic solvents, which are high-boiling-point, weak solvents, for the purpose of increasing coatability. These may be used singly or in a mixture of at least two kinds.

A resist composition according to the present invention is one containing a dissolution inhibitor, of which solubility in alkali aqueous solution changes by the action of acid, and the polymer compound or one in which a dissolution inhibitor is built in the polymer compound. These are particularly suitable as positive-type resist materials. They are also suitable as positive-type resists for 248 nm KrF or 193 nm ArF excimer laser or vacuum ultraviolet (typically 157 nm) region $F_2$ laser, electron beam resists, and resists for X-ray, which correspond to a recent trend for finer semiconductors. In other words, the dissolution inhibitor, of which solubility in alkali aqueous solution changes by the action of acid, is such that at least one of hexafluorocarbinol groups becomes an acid-labile group. It can be used without a particular limitation in its structure. General acid-labile groups are the above-mentioned acid-labile groups, and they are functional groups that are severed by acids. The polymer compound using such dissolution inhibitor is insoluble or scarcely soluble in alkali aqueous solution prior to the activating energy ray irradiation. It is hydrolyzed by an acid generated from an acid generator by the activating energy ray irradiation and thereby shows solubility in alkali aqueous solution.

The photoacid generator used in the composition of the present invention is not particularly limited, and an arbitrary one can be selected from those used as acid generators of chemically amplified resists and then used. As examples of such acid generators, there are cited bissulfonyldiazomethanes, nitrobenzyl derivatives, onium salts, halogen-containing triazine compounds, cyano group-containing oximesulfonate compounds, and other oximesulfonate compounds. These acid generators may be used singly or in a combination of at least two kinds. Its content is generally selected in a range of 0.5 to 20 parts by weight relative to 100 parts by weight of the polymer compound. If this amount is less than 0.5 parts by weight, image formation capability is insufficient. If it exceeds 20 parts by weight, it is difficult to form a homogeneous solution. With this, storage stability tends to be lowered.

A conventional resist pattern forming method is used as a method for using the resist of the present invention. To preferably conduct it, firstly a solution of the resist composition is applied to a supporting member such as silicon wafer with a spinner, followed by drying to form a photosensitive layer. This is exposed to an excimer laser light by an exposure apparatus or the like through a desired mask pattern, followed by heating. Then, this is subjected to a development treatment using a developing solution, for example, an alkali aqueous solution such as 0.1-10 wt % tetramethylammonium hydroxide aqueous solution. This forming method makes it possible to obtain a pattern conforming to the mask pattern.

In the applied field of the present invention, according to need, it is possible to contain a miscible additives, for example, various additives such as additional resins, quencher, plasticizer, stabilizer, coloring agent, surfactant, tackifier, leveling agent, deforming agent, compatibility enhancing agent, adhesion enhancing agent, and antioxidant.

Next, the present invention is explained in more detail by examples. The present invention is, however, not limited to the examples.

Example 1

Synthesis of Compound (3)

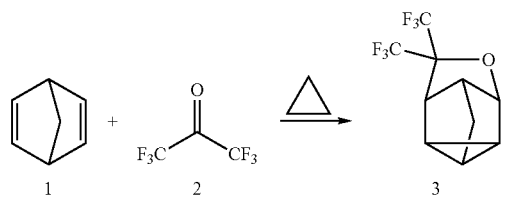

2,5-norbornadiene (1) (220 g) was put into a 2,000 ml autoclave made of SUS, followed by sealing. Hexafluoroacetone (396 g) was weighed and put into this, followed by heating with an oil bath of 130° C. and stirring for 16 hr. After the reaction, the autoclave was cooled down, followed by taking the contents (609 g) out. This was subjected to a distillation under reduced pressure, thereby obtaining a distillate (a colorless transparent liquid, 585 g) of 63° C./10 mmHg. This one was found by nuclear magnetic resonance spectrum (NMR) and mass spectrometer (MS) to be the compound 3. The yield based on 2,5-norbornadiene (1) was 94.5%.

Property Data $^1$H NMR (CDCl$_3$, TMS standard)

δ: 1.43-1.47 (m, 2H), 1.54-1.58 (m, 1H), 1.68-1.72 (m, 2H), 2.52 (s, 1H), 2.79 (s, 1H), 4.58 (s, 1H)

$^{19}$F NMR (CDCl$_3$, CFCl$_3$ standard)

δ: −75.38 (q, 3F, J=10.9 Hz), −69.12 (q, 3F, J=10.9 Hz)

MS(EI): m/e 258 (M$^+$), 189 (M$^+$-CF3), 91 (M$^+$-(CF3)2COH)

Example 2

Synthesis of Compound (4)

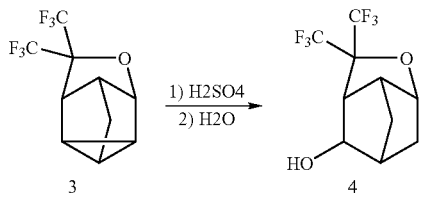

Under nitrogen gas flow, sulfuric acid (26.6 g) was put into a 300 ml flask equipped with a reflux condensing tube, a dropping funnel, a thermometer and a stirrer, followed by cooling a bottom portion of the flask in an iced water bath. The compound (3) (35 g) was put into the dropping funnel, and it was added dropwise in a manner that the temperature of the reaction solution does not exceed 30° C. After the termination of the dropping, stirring was further continued at room temperature for 1 hr. Next, the bottom portion of the flask was again cooled down in the iced water bath, and water (100 ml) was slowly added dropwise from the dropping funnel. After the termination of the dropping, the iced water bath was replaced with an oil bath, following by increasing the temperature, and stirring was conducted at reflux temperature for 1 hr. After the termination of the reaction, it was cooled down to room temperature. It was separated into two phases, and the organic phase of the underlayer was taken out. After washing the organic phase with water, it was dried with magnesium sulfate. The obtained solution was concentrated under reduced pressure, followed by distillation under reduced pressure, thereby obtaining a distillate (24.9 g) of 89° C./1 mmHg. This one turned into white-color crystals at room temperature. This one was found by an analysis by NMR and MS to be the compound (4).

Property Data $^1$H NMR (CDCl$_3$, TMS standard)

δ: 1.23 (d, 1H, J=14.4 Hz), 1.37 (d, 1H, J=10.8 Hz), 1.64-1.73 (m, 1H), 2.09 (d, 1H, J=10.8 Hz), 2.22 (s, 1H), 2.51 (d, 1H, J=4.4 Hz), 3.04 (s, 1H), 4.17 (s, 1H), 4.41 (s, 1H), 4.66-4.72 (m, 1H)

$^{19}$F NMR (CDCl$_3$, CFCl$_3$ standard)

δ: −75.39 (q, 3F, J=11.9 Hz), −66.93 (q, 3F, J=11.9 Hz)

MS(EI): m/e 276 (M$^+$), 258 (M$^+$-H2O), 207 (M$^+$-CF3), 189 (M$^+$-H2O—CF3), 109 (M$^+$-(CF3)2COH)

Example 3

Synthesis of Compound (6)

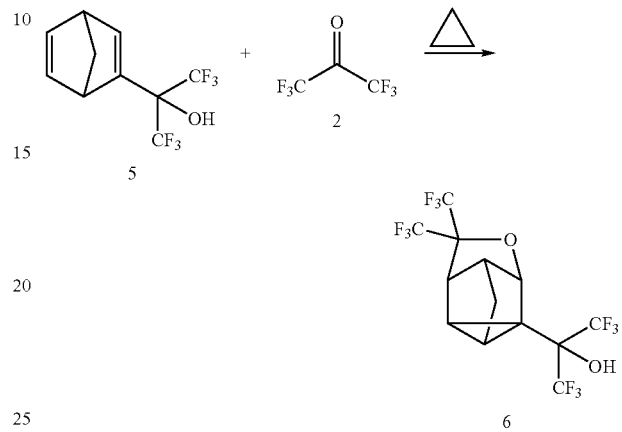

2-(5-bicyclo[2.2.1]-2,5-heptadienyl)-1,1,1-trifluoro-2-(trifluoromethyl)-2-propanol (5) (20 g) was put into a 150 ml autoclave made of SUS, followed by sealing. Hexafluoroacetone (18 g) was weighed and put into this, followed by heating with an oil bath of 150° C. and stirring for 24 hr. After the reaction, the autoclave was cooled down, followed by taking the contents (27 g) out. The obtained solution was concentrated under reduced pressure, followed by purification using a silica-gel column chromatography (hexane:diethyl ether=20:80-50:50), thereby obtaining the compound (6) (19 g). The structure was determined from NMR and MS.

Property Data $^1$H NMR (deuterated acetone, TMS standard)

δ: 1.86 (dt, 1H, J=12.0 Hz and 1.6 Hz), 1.90 (dt, 1H, J=12.0 Hz and 1.6 Hz), 2.05 (m, 1H), 2.21 (m, 1H), 2.82 (brs, 1H), 3.18 (t, 1H, J=2.0 Hz), 4.94 (brs, 1H), 6.40 (s, 1H)

$^{19}$F NMR (deuterated acetone, CFCl$_3$ standard)

δ: −74.18 (d, 3F, J=6.4 Hz), −73.53 (t, 3F, J=9.0 Hz), −72.59 (q, 3F, J=12.0 Hz), −67.65 (s, 3F)

MS(EI): m/e 424 (M$^+$), 355 (M$^+$-CF3), 257 (M$^+$-(CF3)2COH)

Example 4

Synthesis of Compound (7)

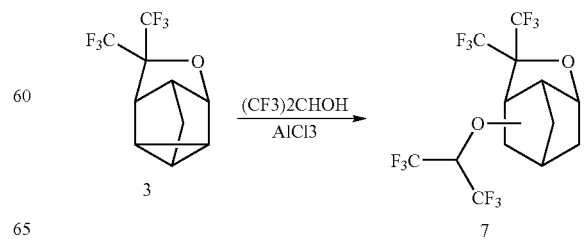

A 1,000 ml autoclave made of SUS was charged with the compound (1) (30 g), hexafluoroisopropanol (HFIP) (100 g), and $AlCl_3$ (0.8 g), followed by stirring for 2 hr under an oil bath temperature of 140° C. After the termination of the reaction, the reaction solution was added to water. To this, diethyl ether was added to have a two-layer separation. Then, the organic layer was washed one time with saturated brine, followed by drying with magnesium sulfate. This solution was filtered and concentrated under reduced pressure, thereby obtaining the compound (4) (44 g) as a mixture of three kinds of isomers (7a, 7b and 7c). The structure was determined by an analysis with NMR and MS.

Property Data

Compound (7a)

$^1$H NMR (deuterated acetone, TMS standard)

δ: 1.25 (dd, 1H, J=14.8 Hz and 2.8 Hz), 1.76 (ddd, 1H, J=12.4 Hz, 8.0 Hz and 4.4 Hz), 1.85 (ddd, 1H, J=12.4 Hz, 8.0 Hz and 4.4 Hz), 1.98 (m, 1H), 2.78 (d, 1H, J=4.4 Hz), 2.83 (s, 1H), 3.17 (m, 1H), 4.43 (s, 1H), 4.78 (dd, 1H, J=7.2 Hz and 4.4 Hz), 5.25 (septet, 1H, J=6.4 Hz)

$^{19}$F NMR (deuterated acetone, $CFCl_3$ standard)

δ: −75.33 (q, 3F, J=10.2 Hz), −73.69 (q, 3F, J=10.2 Hz)

MS(EI): m/e 426 ($M^+$), 407 ($M^+$-F), 357 ($M^+$-CF3), 259 ($M^+$-OCH(CF3)2)

Compound (7b)

$^1$H NMR (deuterated acetone, TMS standard)

δ: 1.24 (dd, 1H, J=14.8 Hz and 3.2 Hz), 1.66 (td, 1H, J=11.6 Hz, and 1.6 Hz), 1.77 (ddd, 1H, J=14.4 Hz, 8.4 Hz and 4.0 Hz), 1.90 (m, 1H), 2.54 (brs, 1H), 2.93 (dd, 1H, J=10.8 Hz and 4.4 Hz), 3.20 (brs, 1H), 3.94 (s, 1H), 4.53 (d, 1H, J=4.8 Hz), 5.29 (septet, 1H, J=6.4 Hz)

$^{19}$F NMR (deuterated acetone, $CFCl_3$ standard)

δ: −74.06 (q, 3F, J=9.4 Hz), −67.43 (q, 3F, J=9.4 Hz)

MS(EI): m/e 426 ($M^+$), 357 ($M^+$-CF3), 259 ($M^+$-OCH(CF3)2)

Compound (7c)

$^1$H NMR (deuterated acetone, TMS standard)

δ: 1.09 (d, 1H, J=14.4 Hz), 1.77 (dd, 1H, J=15.2 Hz and 5.2 Hz), 1.83 (dd, 1H, J=14.0 Hz and 6.0 Hz), 2.07 (dd, 1H, J=14.8 Hz and 6.4 Hz), 2.80 (d, 1H, J=5.6 Hz), 2.94 (s, 1H), 2.98 (m, 1H), 4.15 (d, 1H, J=6.4 Hz), 4.53 (s, 1H), 5.20 (septet, 1H, J=6.4 Hz)

$^{19}$F NMR (deuterated acetone, $CFCl_3$ standard)

δ: −73.86 (q, 3F, J=12.0 Hz), −67.33 (q, 3F, J=12.0 Hz)

MS(EI): m/e 426 ($M^+$), 357 ($M^+$-CF3), 259 ($M^+$-OCH(CF3)2)

Example 5

Synthesis of Compound (9)

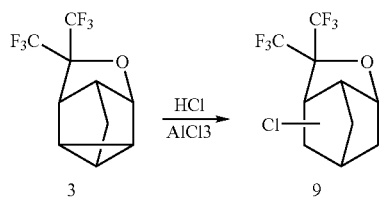

The compound (3) (51 g) and $AlCl_3$ (1.3 g) were put into a 1,000 ml autoclave made of SUS, followed by sealing. Hydrogen chloride gas (20 g) was weighed and put into this, followed by heating with an oil bath of 135° C. and stirring for 2 hr. After the reaction, the autoclave was cooled down, followed by adding the reaction solution to iced water (300 ml) and then extraction by adding diethyl ether (200 ml). The organic phase was washed with water, followed by drying with magnesium sulfate. The obtained solution was concentrated under reduced pressure, followed by distillation under reduced pressure to obtain a distillate (44.4 g) of 53-57.5° C./1.2 mmHg. This one was found by analysis with NMR and MS to be a mixture of four kinds of isomers (9a, 9b, 9c and 9d) of the compound (9).

Property Data

Compound 9a $^1$H NMR (deuterated acetone, TMS standard)

δ: 1.42 (ddd, 1H, J=14.4 Hz, 3.2 Hz and 0.8 Hz), 1.61 (dd, 1H, J=11.2 Hz and 1.2 Hz), 1.95 (m, 1H), 2.16 (dq, 1H, J=11.2 Hz and 1.6 Hz), 2.47 (m, 1H), 3.00 (d, 1H, J=4.4 Hz), 3.21 (m, 1H), 4.39 (s, 1H), 4.80 (dd, 1H, J=8.4 Hz and 4.8 Hz)

$^{19}$F NMR (deuterated acetone, $CFCl_3$ standard)

δ: −75.27 (q, 3F, J=10.2 Hz), −67.09 (q, 3F, J=10.2 Hz)

MS(EI): m/e 294 ($M^+$), 275 ($M^+$-F), 259 ($M^+$-Cl)

Compound 9b $^1$H NMR (deuterated acetone, TMS standard)

δ: 1.71 (dq, 1H, J=11.2 Hz and 1.6 Hz), 1.85 (m, 1H), 2.05 (m, 2H), 2.35 (m, 1H), 2.97 (dd, 1H, J=10.8 Hz and 4.4 Hz), 3.21 (m, 1H), 3.86 (d, 1H, J=2.0 Hz), 4.67 (d, 1H, J=5.2 Hz)

$^{19}$F NMR (deuterated acetone, $CFCl_3$ standard)

δ: −75.23 (q, 3F, J=10.3 Hz), −67.27 (q, 3F, J=10.3 Hz)

MS(EI): m/e 294 ($M^+$), 259 ($M^+$-Cl)

Compound 9c $^1$H NMR (deuterated acetone, TMS standard)

δ: 1.61 (dd, 1H, J=15.2 Hz and 7.2 Hz), 2.05 (m, 3H), 2.36 (m, 1H), 3.04 (dd, 1H, J=10.4 Hz and 3.6 Hz), 3.21 (m, 1H), 4.40 (d, 1H, J=1.6 Hz), 4.94 (dd, 1H, J=7.2 Hz and 5.2 Hz)

$^{19}$F NMR (deuterated acetone, $CFCl_3$ standard)

δ: −75.56 (q, 3F, J=10.2 Hz), −67.25 (q, 3F, J=10.2 Hz),

MS(EI): m/e 294 ($M^+$), 259 ($M^+$-Cl)

Compound 9d $^1$H NMR (deuterated acetone, TMS standard)

δ: 1.62 (dd, 1H, J-14.4 Hz and 0.4 Hz), 1.95 (m, 2H), 2.47 (m, 1H), 2.83 (s, 1H), 3.07 (dd, 1H, J=10.4 Hz and 4.0 Hz), 3.21 (m, 1H), 4.22 (s, 1H), 4.75 (dd, 1H, J=7.2 Hz and 5.2 Hz)

$^{19}$F NMR (deuterated acetone, $CFCl_3$ standard)

δ: −75.32 (q, 3F, J=11.2 Hz), −67.27 (q, 3F, J=11.2 Hz)

MS(EI): m/e 294 ($M^+$), 259 (M+—Cl)

Example 6

Synthesis of Compound (10)

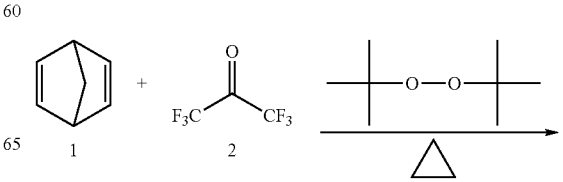

-continued

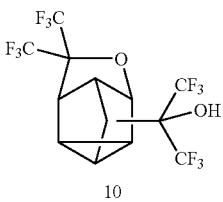

10

2,5-norbornadiene (1) (55.5 g) and di-t-butylperoxide (8.8 g) were put into a 1,000 ml autoclave made of SUS, followed by sealing. Hexafluoroacetone (300 g) was weighed and put into this, followed by heating with an oil bath of 150° C. and stirring for 48 hr. After the reaction, the autoclave was cooled down, followed by taking the contents out. This was subjected to a distillation under reduced pressure, thereby obtaining a distillate (40.0 g) of 55° C./1 mmHg. This one was found by analysis with NMR and MS to be a mixture of two kinds of isomers (10a and 10b) of the compound (10).

Even in case that the compound (3) in place of 2,5-norbornadiene (1) was used in this reaction to conduct a similar reaction, the compound (10) was obtained with almost similar yield and isomer ratio.

Property Data

Compound 10a $^1$H NMR (deuterated acetone, TMS standard)

δ: 1.64 (dd, 1H, J=5.2 Hz and 2.0 Hz), 1.74 (dd, 1H, J=5.6 Hz and 2.4 Hz), 1.79 (m, 1H), 2.84 (brs, 1H), 3.23 (t, 1H, J=2.2 Hz), 5.03 (brs, 1H), 7.02 (s, 1H)

$^{19}$F NMR (deuterated acetone, CFCl$_3$ standard)

δ: −74.41 (d, 3F, J=11.3 Hz), −74.33 (q, 3F, J=12.4 Hz), −74.10 (q, 3F, J=9.0 Hz), −67.88 (q, 3F, J=11.3 Hz)

MS(EI): m/e 424 (M$^+$), 355 (M$^+$-CF3), 257 (M$^+$-(CF3)2COH)

Compound 10b $^1$H NMR (deuterated acetone, TMS standard)

δ: 1.58-1.63 (m, 1H), 1.67-1.73 (m, 1H), 1.85 (m, 1H), 2.75 (brs, 1H), 3.35 (t, J=2.2 Hz, 1H), 4.82 (brs, 1H), 6.96 (s, 1H)

$^{19}$F NMR (deuterated acetone, CFCl$_3$ standard)

δ: −74.82 (q, 3F, J=10.5 Hz), −74.57 (q, 3F, J=10.2 Hz), −73.89 (q, 3F, J=10.2 Hz), −68.26 (q, 3F, J=11.3 Hz)

MS(EI): m/e 424 (M$^+$), 355 (M$^+$-CF3), 257 (M$^+$-(CF3)2C(OH))

Example 7

Synthesis of Compound (11)

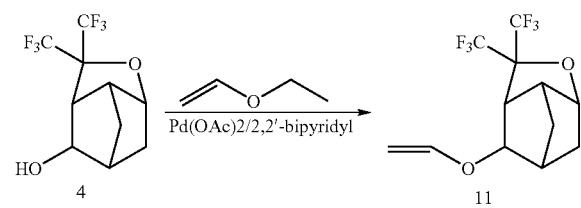

Under nitrogen gas flow, the compound (4) (10.5 g) was put into a 300 ml flask equipped with a reflux condensing tube, a dropping funnel, a thermometer and a stirrer, followed by dissolution by adding ethyl vinyl ether (54.8 g). Herein, palladium acetate (428 mg) and 2,2'-bipyridyl (0.36 g) were added, followed by stirring at room temperature for 47 hr.

After the termination of the reaction, diethyl ether (100 ml) was added to the reaction solution, followed by filtration with CELITE. The filtrated solution was washed with water, followed by drying with magnesium sulfate. The obtained solution was concentrated under reduced pressure, followed by purification using silica-gel chromatography (hexane:ethyl acetate=95:5 80:20), thereby obtaining the compound (11) (5.5 g) as a mixture of mainly two kinds of isomers (11a and 11b). The ratio of the obtained isomers 11a:11b was about 1:3. The structure was determined from NMR and MS.

Property Data

Compound 11a $^1$H NMR (CDCl$_3$, TMS standard)

δ: 1.33-1.40 (m, 2H), 1.64-1.72 (m, 1H), 1.97-2.03 (m, 1H), 2.46 (s, 1H), 2.68 (d, 1H, J=4.4 Hz), 3.10 (m, 1H), 4.12 (dd, 1H, 6.4 Hz and 1.8 Hz), 4.27 (s, 1H), 4.37 (dd, 1H, 14.0 Hz and 1.8 Hz), 4.64-4.69 (m, 1H), 6.27 (dd, 1H, J=14.0 Hz and 6.4 Hz)

$^{19}$F NMR (CDCl$_3$, CFCl$_3$ standard)

δ: −76.30 (q, 3F, J=10.8 Hz), −68.03 (q, 3F, J=10.8 Hz),

Compound 11b $^1$H NMR (CDCl$_3$, TMS standard)

δ: 1.33-1.53 (m, 2H), 1.70-1.85 (m, 1H), 1.90-1.96 (m, 1H), 2.38 (s, 1H), 2.72-2.77 (m, 1H), 3.10 (m, 1H), 3.86 (s, 1H), 4.12 (dd, 1H, 6.8 Hz and 2.0 Hz), 4.27 (dd, 1H, 14.4 Hz and 2.0 Hz), 4.38-4.44 (m, 1H), 6.33 (dd, 1H, J=14.4 Hz and 6.8 Hz)

$^{19}$F NMR (CDCl$_3$, CFCl$_3$ standard)

δ: −76.35 (q, 3F, J=10.8 Hz), −68.36 (q, 3F, J=10.8 Hz)

Example 8

Synthesis of Compound (12)

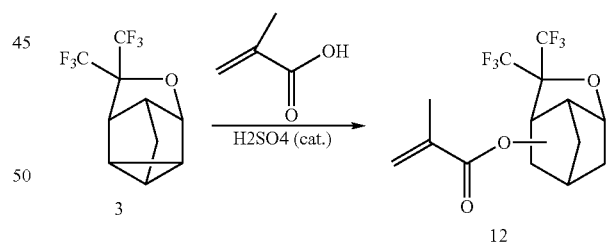

A 300 ml flask equipped with a reflux condensing tube, a dropping funnel, a thermometer and a stirrer was charged with the compound (3) (10.0 g), methacrylic acid (5.0 g) and concentrated sulfuric acid (0.2 g), followed by stirring for 5 hr in an oil bath of 150° C. After the termination of the reaction, the reaction solution was put into a saturated aqueous solution of calcium carbonate, followed by adding diethyl ether to achieve a two-phase separation. The organic phase was washed with saturated brine. The obtained solution was dried with magnesium sulfate, followed by filtration and concentration, thereby obtaining the compound (12) (7.2 g) as a mixture of four kinds of isomers (12a, 12b, 12c and 12d). The structure was determined from NMR and MS.

Property Data

Compound 12a $^1$H NMR (deuterated acetone, TMS standard)

δ: 1.38 (dd, 1H, J=15.6 Hz and 3.2 Hz), 1.53 (d, 1H, J=11.2 Hz), 1.82 (m, 1H), 1.92 (q, 3H, J=0.8 Hz), 2.01 (dq, 1H, J=12.0 Hz and 2.0 Hz), 2.82 (s, 1H), 2.89 (d, 1H, J=4.4 Hz), 3.19 (m, 1H), 4.80 (dd, 1H, J=7.2 and 6.4 Hz), 5.29 (s, 1H), 5.67 (m, 1H), 6.14 (m, 1H)

$^{19}$F NMR (deuterated acetone, CFCl$_3$ standard)

δ: −75.18 (q, 3F, J=11.5 Hz), −67.28 (q, 3F, J=11.5 Hz)

MS(EI): m/e 344 (M$^+$), 329 (M$^+$-CH3)

Compound 12b $^1$H NMR (deuterated acetone, TMS standard)

δ: 1.25 (d, 1H, J=14.4 Hz), 1.75 (dd, 1H, J=15.2 Hz and 5.2 Hz), 1.88 (dd, 1H, J=13.2 Hz and 5.6 Hz), 1.91 (q, 3H, J=0.8 Hz), 2.09 (dd, 1H, J=15.2 Hz and 6.4 Hz), 2.63 (d, 1H, J=4.8 Hz), 2.98 (m, 1H), 3.05 (brs, 1H), 4.56 (brs, 1H), 4.80 (d, 1H, J=6.4 Hz), 5.64 (m, 1H), 6.10 (m, 1H)

$^{19}$F NMR (deuterated acetone, CFCl$_3$ standard)

δ: −74.14 (q, 3F, J=12.2 Hz), −69.51 (q, 3F, J=12.2 Hz)

MS(EI): m/e 344 (M$^+$), 325 (M$^+$-F), 258 (M$^+$-CH3CCH2CO2H)

Compound 12c $^1$H NMR (deuterated acetone, TMS standard)

δ: 1.43 (m, 1H), 1.65 (m, 1H), 1.73 (m, 1H), 1.92 (m, 3H), 1.95 (m, 1H), 2.40 (brs, 1H), 2.95 (m, 1H), 3.05 (brs, 1H), 4.53 (d, 1H, J=5.6 Hz), 4.65 (brs, 1H), 5.65 (m, 1H), 6.08 (m, 1H)

$^{19}$F NMR (deuterated acetone, CFCl$_3$ standard)

δ: −75.30 (q, 3F, J=11.3 Hz), −67.28 (q, 3F, J=11.3 Hz),

MS(EI): m/e 344 (M$^+$), 325 (M$^+$-F), 276 (M$^+$-CH3CCH2CO)

Compound 12d $^1$H NMR (deuterated acetone, TMS standard)

δ: 1.21 (m, 1H), 1.67 (m, 1H), 1.76 (m, 1H), 1.90 (m, 1H), 1.92 (m, 3H), 2.49 (brs, 1H), 2.97 (m, 1H), 3.20 (brs, 1H), 4.61 (m, 1H), 4.75 (m, 1H), 5.65 (m, 1H), 6.10 (m, 1H)

$^{19}$F NMR (deuterated acetone, CFCl$_3$ standard)

δ: −74.35 (q, 3H, J=11.5 Hz), −68.01 (q, 3H, J=11.5 Hz)

MS(EI): m/e 344 (M$^+$), 276 (M$^+$-CH3CCH2CO)

Example 9

Polymer of Compound (12)

Under nitrogen gas flow, a flask equipped with a reflux condensing tube and a stirrer was charged with the compound (12) (10.0 g),

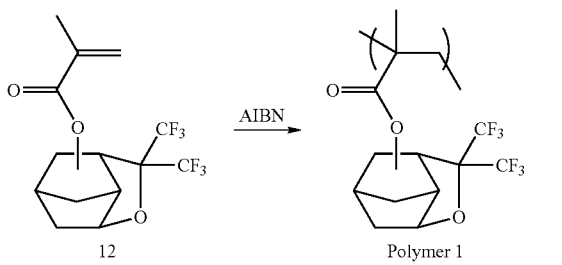

n-butyl acetate (20.0 g) and AIBN (150 mg), followed by stirring for 20 hr under heating with an oil bath of 60° C.

After the termination of the reaction, it was added to n-hexane (400 ml), followed by stirring. The resulting precipitate was taken out by filtration. This was subjected to a vacuum drying at 50° C. for 18 hr, thereby obtaining a polymer (the polymer 1) (8.9 g) of a white-color solid. The structure was confirmed by NMR. The molecular weight (Mw and Mw/Mn) was determined from gel permeation chromatography (GPC, standard polystyrene). The results are shown in Table 1.

Example 10

Copolymer of the Compound (12) and Methyladamantylmethacrylate

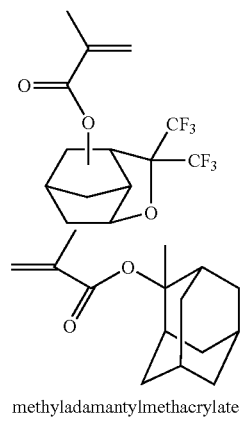

methyladamantylmethacrylate

Under nitrogen gas flow, a flask equipped with a reflux condensing tube and a stirrer was charged with the compound (12) (7.2 g), methyladamantylmethacrylate (2.8 g), n-butyl acetate (20.0 g) and AIBN (150 mg), followed by stirring for 20 hr under heating with an oil bath of 60° C. After the termination of the reaction, it was added to n-hexane (400 ml), followed by stirring. The resulting precipitate was taken out by filtration. This was subjected to a vacuum drying at 50° C. for 18 hr, thereby obtaining a polymer (the polymer 2) (8.0 g) of a white-color solid. The structure was confirmed by NMR. The molecular weight (Mw and Mw/Mn) was determined from gel permeation chromatography (GPC, standard polystyrene). The results are shown in Table 1.

Example 11

Copolymer of the Compound (12), Methyladamantylmethacrylate and Maleic Anhydride

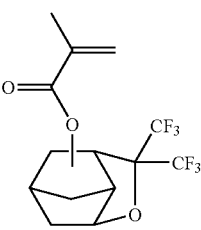

-continued

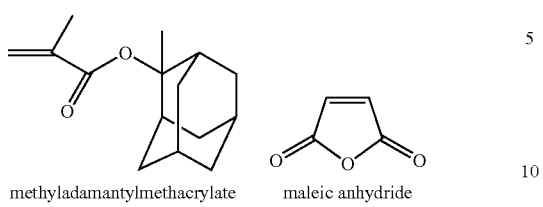

methyladamantylmethacrylate    maleic anhydride

Under nitrogen gas flow, a flask equipped with a reflux condensing tube and a stirrer was charged with the compound (12) (6.4 g), methyladamantylmethacrylate (2.6 g), maleic anhydride (1.0 g), n-butyl acetate (20.0 g) and AIBN (150 mg), followed by stirring for 20 hr under heating with an oil bath of 60° C. After the termination of the reaction, it was added to n-hexane (400 ml), followed by stirring. The resulting precipitate was taken out by filtration. This was subjected to a vacuum drying at 50° C. for 18 hr, thereby obtaining a polymer (the polymer 3) (7.3 g) of a white-color solid. The structure was confirmed by NMR. The molecular weight (Mw and Mw/Mn) was determined from gel permeation chromatography (GPC, standard polystyrene). The results are shown in Table 1.

Example 12

Copolymer of the Compound (11) and T-Butyl α-Trifluoromethylacrylate

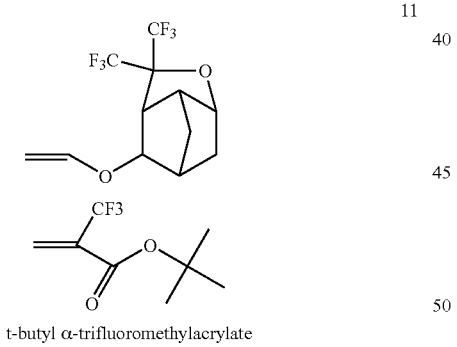

t-butyl α-trifluoromethylacrylate

Under nitrogen gas flow, a flask equipped with a reflux condensing tube and a stirrer was charged with the compound (11) (3.5 g), t-butyl α-trifluoromethylacrylate (2.5 g), n-butyl acetate (6.0 g) and AIBN (200 mg), followed by stirring for 20 hr under heating with an oil bath of 60° C. After the termination of the reaction, it was added to n-hexane (400 ml), followed by stirring. The resulting precipitate was taken out by filtration. This was subjected to a vacuum drying at 50° C. for 18 hr, thereby obtaining a polymer (the polymer 4) (5.3 g) of a white-color solid. The structure was confirmed by NMR. The molecular weight (Mw and Mw/Mn) was determined from gel permeation chromatography (GPC, standard polystyrene). The results are shown in Table 1.

Example 13

Copolymer of the Compound (11), Methacrylonitrile and T-Butyl α-Trifluoromethylacrylate

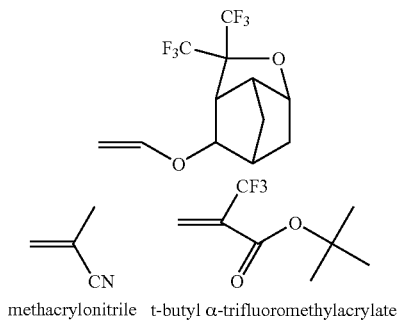

methacrylonitrile  t-butyl α-trifluoromethylacrylate

Under nitrogen gas flow, a flask equipped with a reflux condensing tube and a stirrer was charged with the compound (11) (4.0 g), methacrylonitrile (0.3 g), t-butyl α-trifluoromethylacrylate (1.7 g), n-butyl acetate (6.0 g) and AIBN (150 mg), followed by stirring for 20 hr under heating with an oil bath of 60° C. After the termination of the reaction, it was added to n-hexane (400 ml), followed by stirring. The resulting precipitate was taken out by filtration. This was subjected to a vacuum drying at 50° C. for 18 hr, thereby obtaining a polymer (the polymer 5) (4.8 g) of a white-color solid. The structure was confirmed by NMR. The molecular weight (Mw and Mw/Mn) was determined from gel permeation chromatography (GPC, standard polystyrene). The results are shown in Table 1.

Example 14

Copolymer of the Compound (11), T-Butyl α-Trifluoromethylacrylate and 3,5-HFA-ST

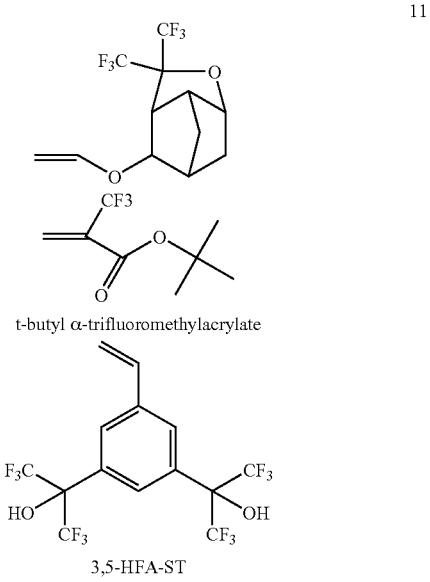

t-butyl α-trifluoromethylacrylate 3,5-HFA-ST

Under nitrogen gas flow, a flask equipped with a reflux condensing tube and a stirrer was charged with the compound (11) (3.0 g), t-butyl α-trifluoromethylacrylate (4.8 g), 3,5-HFA-ST (6.5 g), n-butyl acetate (15.0 g) and AIBN (200 mg), followed by stirring for 20 hr under heating with an oil bath of 60° C. After the termination of the reaction, it was added to n-hexane (400 ml), followed by stirring. The resulting precipitate was taken out by filtration. This was subjected to a vacuum drying at 50° C. for 18 hr, thereby obtaining a polymer (the polymer 6) (7.7 g) of a white-color solid. The structure was confirmed by NMR. The molecular weight (Mw and Mw/Mn) was determined from gel permeation chromatography (GPC, standard polystyrene). The results are shown in Table 1.

Example 15

Copolymer of the Compound (11), T-Butyl α-Trifluoromethylacrylate and Octafluorocyclopentene

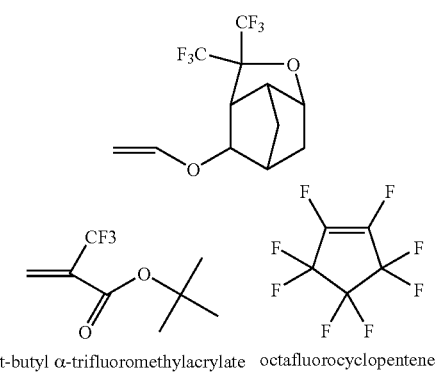

Under nitrogen gas flow, a flask equipped with a reflux condensing tube and a stirrer was charged with the compound (11) (3.0 g), t-butyl α-trifluoromethylacrylate (4.8 g), octafluorocyclopentene (3.2 g), n-butyl acetate (11.0 g) and AIBN (200 mg), followed by stirring for 20 hr under heating with an oil bath of 60° C. After the termination of the reaction, it was added to n-hexane (400 ml), followed by stirring. The resulting precipitate was taken out by filtration. This was subjected to a vacuum drying at 50° C. for 18 hr, thereby obtaining a polymer (the polymer 7) (4.3 g) of a white-color solid. The structure was confirmed by NMR. The molecular weight (Mw and Mw/Mn) was determined from gel permeation chromatography (GPC, standard polystyrene). The results are shown in Table 1.

Example 16

Copolymer of the Compound (11) and TFMA-3,5-HFA-CHOH-MOM

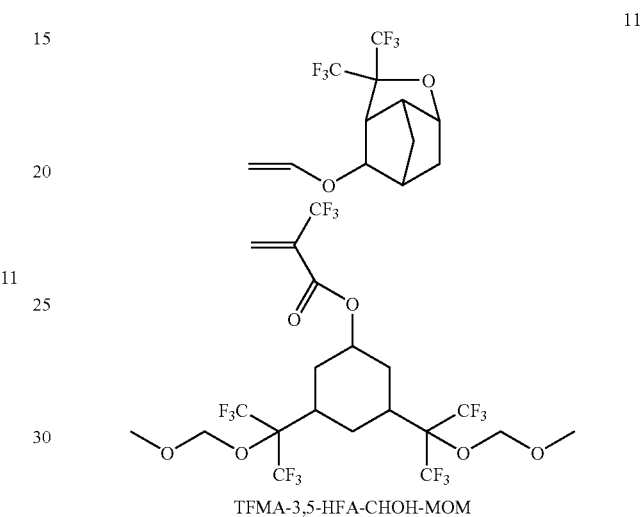

Under nitrogen gas flow, a flask equipped with a reflux condensing tube and a stirrer was charged with the compound (11) (3.0 g), TFMA-3,5-HFA-CHOH-MOM (6.3 g), n-butyl acetate (18.6 g) and AIBN (150 mg), followed by stirring for 20 hr under heating with an oil bath of 60° C. After the termination of the reaction, it was added to n-hexane (400 ml), followed by stirring. The resulting precipitate was taken out by filtration. This was subjected to a vacuum drying at 50° C. for 18 hr, thereby obtaining a polymer (the polymer 8) (6.6 g) of a white-color solid. The structure was confirmed by NMR. The molecular weight (Mw and Mw/Mn) was determined from gel permeation chromatography (GPC, standard polystyrene). The results are shown in Table 1.

TABLE 1

| Ex. | Charged Monomers | Formed Polymer (Yield) | Molecular Weight Mw (Mw/Mn) |
|---|---|---|---|
| 9 | Compound 12 (10.0 g) | Polymer 1 (8.9 g) | 33,000 (1.5) |
| 10 | Compound 12 (7.2 g) methyladamantylmethacrylate (2.8 g) | Polymer 2 (8.0 g) | 26,000 (1.5) |
| 11 | Compound 12 (6.4 g) methyladamantylmethacrylate (2.6 g) maleic anhydride (1.0 g) | Polymer 3 (7.3 g) | 20,100 (1.4) |
| 12 | Compound 11 (3.5 g) t-butyl α-trifluoromethylacrylate (2.5 g) | Polymer 4 (5.3 g) | 51,900 (1.7) |
| 13 | Compound 11 (4.0 g) methacrylonitrile (0.3 g) t-butyl α-trifluoromethylacrylate (1.7 g) | Polymer 5 (4.8 g) | 32,000 (1.6) |
| 14 | Compound 11 (3.0 g) t-butyl α-trifluoromethylacrylate (4.8 g) 3,5-HFA-ST (6.5 g) | Polymer 6 (7.7 g) | 27,000 (1.6) |

TABLE 1-continued

| Ex. | Charged Monomers | Formed Polymer (Yield) | Molecular Weight Mw (Mw/Mn) |
|---|---|---|---|
| 15 | Compound 11 (3.0 g) t-butyl α-trifluoromethylacrylate (4.8 g) octafluorocyclopentene (3.2 g) | Polymer 7 (4.3 g) | 14,000 (1.5) |
| 16 | Compound 11 (3.0 g) TFMA-3,5-HFA-CHOH-MOM (6.3 g) | Polymer 8 (6.6 g) | 19,000 (1.4) |

Example 17

The polymer compounds of Examples 9-16 were dissolved in propylene glycol methyl acetate, and they were adjusted to having a solid matter concentration of 14%. Then, triphenylsulfonium triflate (TPS105) made by Midori Kagaku Co., Ltd. as an acid generator was dissolved in a manner to be 2 parts by weight per 100 parts by weight of the polymer compound, thereby preparing two kinds of resist solutions. These were subjected to spin coating. By a measurement of light transmittance of a film thickness of 100 nanometers at a wavelength of 157 nm, they were respectively 52%, 38%, 35%, 50%, 55%, 57%, 72% and 67% to Examples 9, 10, 11, 12, 13, 14, 15 and 16, showing high transparency in vacuum ultraviolet wavelength region.

Then, all of the resist solutions were filtered with a membrane filer (pore diameter: 0.2 μm). Then, each composition solution was applied to a silicon wafer by spin coating to obtain a resist film of a film thickness of 250 nanometers. After conducting a preliminary baking at 120° C., an exposure to a 248 nm ultraviolet ray was conducted through a photomask. Then, a post exposure baking was conducted at 130° C. Then, a development was conducted at 23° C. for 1 minute using 2.38 wt % tetramethylammonium hydroxide aqueous solution. As a result, a high resolution pattern was obtained from each resist solution. There were almost not found inferiority defect in adhesion to substrate, film-forming inferiority defect, development defect and etching resistance inferiority defect.

The invention claimed is:

1. A fluorine-containing cyclic compound represented by the following formula (3) or (4)

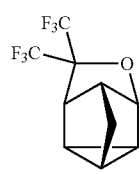

(3)

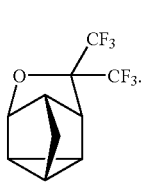

(4)

2. A fluorine-containing cyclic compound represented by one of the following formulas (13) to (16)

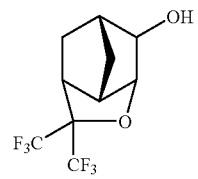

(13)

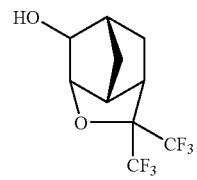

(14)

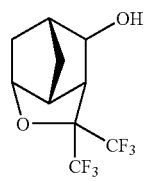

(15)

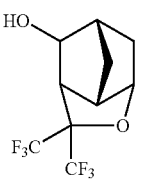

(16)

3. A fluorine-containing polymerizable monomer represented by one of the following formulas (30) to (33)

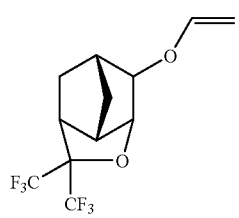

(30)

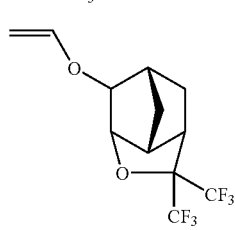

(31)

-continued

(32)
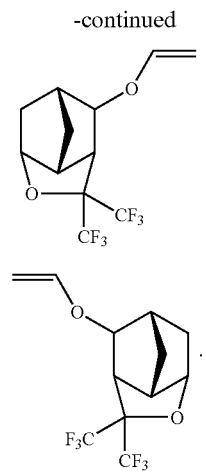

(33)

4. A fluorine-containing polymerizable monomer represented by one of the following formulas (34) to (37),

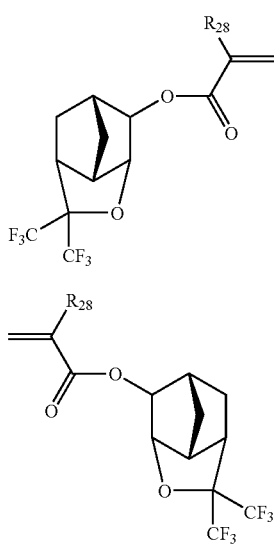

(34)

(35)

-continued

(36)
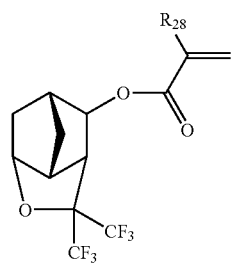

(37)
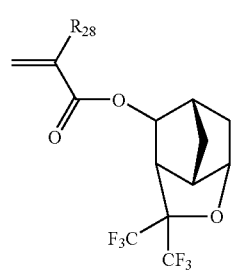

wherein, in the formulas (34) to (37), $R_{28}$ represents a hydrogen, methyl group, fluorine, or trifluoromethyl group.

5. A fluorine-containing polymer compound prepared by a polymerization or copolymerization of at least a fluorine-containing polymerizable monomer according to claim 3.

6. A resist material using a fluorine-containing polymer compound according to claim 5.

7. A fluorine-containing polymer compound prepared by a polymerization or copolymerization of at least a fluorine-containing polymerizable monomer according to claim 4.

8. A resist material using a fluorine-containing polymer compound according to claim 7.

* * * * *